United States Patent [19]
Walton et al.

[11] Patent Number: 5,905,032
[45] Date of Patent: May 18, 1999

[54] ELECTROSYNTHETIC METHOD OF MODIFYING BIOMOLECULES IN PARTICULAR ENZYMES

[75] Inventors: David John Walton, Coventry; John Heptinstall, Kenilworth; Paul Graham Richards, Basingstoke, all of United Kingdom

[73] Assignee: Coventry University, Coventry, United Kingdom

[21] Appl. No.: 08/925,870

[22] Filed: Sep. 9, 1997

Related U.S. Application Data

[63] Continuation of application No. 08/549,740, filed as application No. PCT/GB94/00998, May 9, 1994, abandoned.

[30] Foreign Application Priority Data

Aug. 5, 1993 [GB] United Kingdom .................. 9309513

[51] Int. Cl.$^6$ ............................. C12N 13/00; C25B 3/00; C07K 1/00
[52] U.S. Cl. .................................... 435/173.2; 435/173.1; 204/157.82; 530/345; 530/350; 530/402
[58] Field of Search .......................... 435/106–110, 113, 435/115, 116, 173.1, 173.2; 204/155, 157.82; 530/300, 305, 333, 335, 345, 350, 402

[56] References Cited

U.S. PATENT DOCUMENTS 5,364,851  11/1994  Joran ..................................... 530/345

OTHER PUBLICATIONS

Reynaud et al. Bioelectrochem. and Bioenerg. 1980 pp. 595–606, vol. 7.

Brabec and Mornstein. Biochimica et Biophysica Acta. vol. 625, pp. 43–50, 1980 (ref 1980a).

Brabec and Mornstein. Biophysical Chem. vol. 12, pp. 159–165 1980 (ref 19806).

"Comptes Rendus des Seances de l'Academie des Sciences," Serie II:Mecanique, Physique, Chimie, Sciences de la Terre, Sciences de l'Univers, vol. 301, No. 15, Nov. 14 1985, Montreuil Fr, pp. 1119–1221.

"Electrochemical Oxidation of Proteins as a New Probe of Protein Structure,"Chemical Abstracts, vol.94, No. 25, Jun. 22, 1981, Columbus, Ohio, US; Abstract No. 20411m, V Brabec, p. 187.

"The Electrochemical Oxidation of Three Proteins; RNAse A, Bovine Srum Albumin and Concanavalin A at Solid Electrodes," Chemical Abstracts, vol. 94, No. 9, Mar. 2, 1981, Columbus, Ohio, US; Abstract No. 60173j, p. 245.

"Electrochemical Behavior of Proteins at Graphite electrodes. I. Electrooxidation of Proteins as a New Probe of Protein Structure and Reaction," Chemical Abstracts, vol. 93, ho. 25, Dec. 22, 1980, Columbus, Ohio, US; Abstract No. 234256k, p. 398.

"Electrochemical Behavior of Proteins at Graphite Electrodes. II. Electrooxidation of Amino Acids," Chemical Abstracts, vol. 93, No. 25, Dec. 22, 1980, Columbus, Ohio, US; Abstract No. 233235r, p. 296.

"Proteins Modified by Iodine Isotopes," Chemical Abstracts, vol. 85, No. 25, Dec. 20, 1976, Columbus, Ohio, US; Abstract No. 188160j, p. 178.

*Primary Examiner*—Leon B. Lankford, Jr.
*Assistant Examiner*—Christopher R. Tate
*Attorney, Agent, or Firm*—Oppenheimer Wolff & Donnelly

[57] ABSTRACT

Pendant groups in the alpha-amino acid monomer residues comprising a polypeptide molecule are selectively modified by applying an electric potential across an electrochemical cell containing the polypeptide.

10 Claims, 5 Drawing Sheets

ELECTROSYNTHETIC METHOD OF MODIFYING BIOMOLECULES IN PARTICULAR ENZYMES

This application is a continuation of application Ser. No. 08/549,740 filed Jan. 19, 1996, now abandoned, which is a 371 of PCT/GB94/00998, filed May 9, 1994.

This invention relates to a method of modifying complex organic molecules, in particular proteins such as enzymes or antibodies.

Proteins comprise chains of a-amino acids connected through peptide bonds to form polypeptide molecules of the general formula The amino acid monomers differ in the nature of the pendant groups $R_1, R_2, R_3 \ldots$. In the following, the pendant groups are referred to simply as "R groups".

Techniques for the modification of proteins have substantial significance for the development of chemical, analytical and biotechnological systems. Transformations in the primary, secondary and tertiary structures can modify the catalytic specificity or kinetic properties of an enzyme. Modifications of functional groups can serve as probes of structure and function and the attachment of 'labels' or molecular probes onto biomolecules can lead to the development of powerful analytical and diagnostic tools.

The deliberate manipulation of enzymes to produce novel transformations, enhanced behaviour, greater stability and other benefits is the subject of considerable research effort at present. There are great commercial opportunities for a successful system, in the pharmaceutical, chemical and food industries among others.

Enzymes are protein-based complex biomolecules that undertake specific transformations in biological systems. Enzymology is a complex and expanding discipline, and it is an aim of workers in the field to develop enzyme variants that may have novel properties or enhanced performance characteristics. Desirable properties sought for industrial enzymatic processes include enhanced rate and binding constants, altered reactivity and substrate specificities and increased thermostability and stability in aqueous and non-aqueous solvent systems, or other conditions.

Established techniques for effecting covalent modifications in proteins can be divided into two major categories.
1. Site directed mutagenesis
2. Chemical modifications.

Site directed mutagenesis is based on transformations in the genetic code resulting in an alteration in the sequence of DNA encoded amino acids in the transcribed protein. The methods employed are technically complicated, and the 'mutant' protein may not fold in the same way as the native protein or be processed in the same way. Restrictions may also be imposed by only having a limited pool of amino acids to choose from.

Chemical modifications are easier to perform but difficult to control. There are problems of reproducibility and specificity, the modifications are dependent upon the chemical reactivity and availability of the functional groups on the protein and are difficult to target towards a specific residue. Covalent modification of proteins is mainly confined to the amino acids cysteine, cystine, arginine, lysine, tyrosine, tryptophan, histidine, aspartate, glutamate, serine and threonine.

Proteins have been subjected to electrochemical methods, but these have been largely for analytical purposes. Electrosynthetic methods have also been used, but these have resulted in cleavage of the amino acid chain.

It has now been discovered that electrochemical methods can be used to effect subtle and specific synthetic modifications to protein molecules such as enzymes, and in particular to the pendant "R groups" of such molecules.

According to the present invention, there is provided a method for the selective electrosynthetic modification of one or more R groups (as hereinbefore defined) in a polypeptide molecule, which method comprises the steps of
a) dispersing or dissolving the polypeptide molecule in a suitable medium,
b) placing the dispersion or solution so obtained in an electrochemical cell, and
c) applying an electric potential across the electrochemical cell.

The method according to the invention is advantageous primarily in that it permits the carrying out of subtle and specific modifications to the R group(s) without destroying the integrity of the molecule. The method may therefore be of utility in the synthesis of modified enzymes or other proteins.

Since the method of the present invention is a preparative synthetic method, it may be followed by the subsequent step of isolating and/or purifying the reaction product. For some applications, however, the reaction product may be used in situ, eg where the reaction product is subjected to further chemical treatment.

The modification performed by the method of the invention is preferably an electrooxidation. Amino acid residues which may be susceptible to electrooxidation include cysteine, cystine, arginine, lysine, tyrosine, tryptophan, histidine, aspartate, glutamate, serine and threonine.

It has been found that the electrochemical modifications which occur are highly dependent on the experimental parameters. Particular electrochemical modifications may be performed with a high degree of specificity by appropriate choice of such parameters. Amongst the parameters which may be controlled are electrode potential, electrode material, pH, solvent nature, electrolyte nature and concentration, temperature, pressure, presence of mediators and interactive additives and other well established electrochemical parameters.

As will be apparent from the following description, a protein containing for example two identical amino acids in different positions may be susceptible to electrochemical reaction of one of these amino acids in preference to the other with a high degree of specificity.

By changing the electrode potential, the pH or other well-established parameters quite different electrochemical modification may take place. These effects are referred to in the specific examples set out below.

The method of the invention is preferably carried out at a potential (relative to a standard calomel electrode) of from about 0.6 to 3.0 V, more preferably from about 0.9 to 1.7 V.

Electrochemical methodology can be used to provide transformed intermediates with specific reactive sites. Such species, or derivatives thereof, may be used in, for example, labelling procedures and in immobilisation.

In one particular embodiment, the invention provides a method for the electronitration of tyrosine residues in a tyrosine-containing polypeptide molecule. This reaction may be carried out in alkaline conditions. Good results have been obtained using copper electrodes, especially anodised copper electrodes. Other electrodes such as graphite, nickel and platinum, with appropriate buffer systems (including both nitrogen-containing and nitrogen-free buffer systems), have also been utilised.

The introduction of a nitro group into a tyrosine R group is potentially useful since the nitro group may be reduced by conventional chemical means to an amine moiety of distinctive nucleophilicity. Such an amine moiety may be utilised to label or immobilise the modified tyrosine-containing polypeptide.

Thus, according to a specific aspect of the invention there is provided a method for the electronitration of tyrosine residues in a tyrosine-containing polypeptide molecule, which method comprises the steps of a) dispersing or dissolving the polypeptide molecule in a suitable medium, b) placing the dispersion or solution so obtained in an electrochemical cell, and c) applying an electric potential across the electrochemical cell.

The method may be followed by the further steps of reducing the nitro group introduced into the tyrosine residue and reacting the amino moiety so formed with, for example, a suitable labelling molecule or particle, or the activated surface of a device such as a biosensor.

Apart from tyrosine, other amino acid residues which may be susceptible to electronitration by analogous methods include tryptophan, histidine and methionine.

In another specific embodiment of the invention, methionine-containing polypeptides are oxidised under acidic conditions. The reaction is preferably carried out using graphite electrodes. Preferably, the reaction is performed at a pH of between about 2 and 5, most preferably between about 2 and 4, say a pH of about 3.

The reaction is preferably carried out at a potential of greater than 1.0 V relative to SCE.

The electrodes used may be pre-treated eg by anodisation of copper electrodes.

The method of the invention may be particularly suited to the modification of enzymes. It is envisaged that by modification of the enzyme molecule using the present invention enzymes may be developed capable of operating under different conditions of, for example, temperature and pH or carrying out different catalytic transformations. Further, it may be possible to adhere the enzymes to a support by procedures involving electrochemistry to promote practical usefulness of the enzyme in relevant situations.

The invention may also enable indirect electrochemical transformation to take place. Thus, instead of discharging a group on the enzyme itself, an alternative substrate may be employed to electrogenerate a reactive species which attacks the enzyme.

The range of possible electro-initiated reactions is very wide including substitutions, eliminations, additions, cyclisations and rearrangements. Any of these changes in an enzyme structure could produce changes that significantly affect the properties of the enzyme.

Other types of polypeptide molecule molecule may be susceptible to change by the modification method described above and it is to be understood that the invention is not limited to its application to enzymes.

The invention will now be described in greater detail, by way of illustration only, in the following Examples.

EXAMPLE 1

Anodic Reaction of Tyrosine Residues
Methods
Electrochemical modification of proteins Lysozyme was extensively dialysed against distilled water prior to use. Unless otherwise stated the reaction mixtures (40 ml) contained 0.1% (w/v) protein in 50 mM sodium tetraborate solution (pH 9.5) and were electrooxidised using copper electrodes (20×20×0.1 mm) in a glass cell at 20° C. Electrodes were cut from a copper sheet (BDE AnalaR copper foil) and degreased in warm dichloromethane, followed by immersion in concentrated HCl and finally rinsed with distilled water. Copper anodes and cathodes were used and placed at opposite sides of the cell, parallel with each other. Reaction mixtures were stirred throughout the experiment with a magnetic follower and potentials/currents applied using an EG&G Model 273 Potentiostat/Galvanostat. All potentials were measured relative to a standard calomel electrode (SCE). In order to ensure that the reaction were anodically initiated the cathode was covered with dialysis membrane.

Purification of electrochemically modified lysozyme

Reaction mixtures were dialysed overnight against two liters of distilled water and lyophilised. A weighed amount of product was dissolved in a minimum amount of 20 mM phosphate buffer pH 8.0, filtered using a 0.45 $\mu$m nylon filter and injected directly onto a strong cation exchange h.p.l.c. column (TSK SP-5PW,8×75 mm, supplied by LKB). A linear gradient of 20 mM sodium phosphate pH 8.0 to the same buffer containing 1M NaCl over 60 minutes was used to separate the modified proteins. Elution was monitored by absorbance at 280 nm. The pI values of the modified lysozymes were estimated by weak cation exchange h.p.l.c. using a Protein Pac CM 8HR 10×100 mm column supplied by Waters, and employing the procedure of van den Eijnden-van Raaij et al [High-Performance Liquid Chromatography of Peptides and Proteins: Separation, Analysis, and Conformation (Mant, CT, Hodges RS, eds) pp 239–244 CRC Press Inc. London (1991)].

Gel filtration was performed using a Bio-Gel P6 column (12×50 mm) equilibrated with 10 mM phosphate buffer (pH 8.0) and eluted with the same buffer.

Peptide mapping of lysozyme

A sample of approximately 50 $\mu$g of lysozyme, separated by ion exchange h.p.l.c. was precipitated by the addition of trichloroacetic acid to give a final concentration of 10% (w/v). The sample was incubated on ice for 30 minutes and pelleted in a microcentrifuge, washing twice with 200 $\mu$l of ice cold acetone. The protein pellet was resuspended in 50 $\mu$l of 8M urea, 0.4M ammonium bicarbonate, 50 m dithiothreitol and incubated at 60° C. for 30 minutes under a nitrogen atmosphere. Following incubation, iodoacetic acid was added to give a 1.2 fold molar excess over thiol groups, and left at room temperature for 30 minutes. The solution was diluted to give 2M in urea, and digestion initiated by the addition of 2 µg of trypsin. After overnight incubation at 37° C. a portion of the digest was analysed by reversed phase h.p.l.c. using a Waters Delta Pac $C_{18}$ column (2.1 mm×25 cm). Elution was with a gradient of 2–50% (v/v) acetonitrile containing 0.1% (v/v) trifluoroacetic acid (TFA) or 0.1% (v/v) heptafluorobutyric acid (HFBA) at a flow rate of 150 µl min$^{-1}$ for 1 h, and monitored by absorbance at 206 nm.

Limited proteolysis of lysozyme with lys-C protease was conducted in 7M urea, 0.1M Tris/HCl pH 8.0 overnight at 37° C. The lysozyme sample was prepared as for tryptic digests (usually 50 to 100 µg) and digested with a protese to substrate ratio of 1:100 in 100 µl of buffer. Following digestion dithiothreitol was added to give a final concentration of 100 mM and incubated at 37° C. for 60 minutes. For PAGE analysis a small amount of Coomassie Blue G250 was added and the sample loaded directly in a well of a slab gel. The peptides were separated by Tricine SDS/PAGE using a Protean II xi slab gel (200×160×0.75 mm) supplied by Bio-Rad. Sample loads were approximately 20 µg per lane.

Digestion with V8 protease was conducted in 0.1M Tris/HCl pH 8.0 containing 0.1% (w/v) SDS. The lysozyme sample was prepared as for tryptic digests (usually 50 to 100 µg) and digested with a protease to substrate ratio of 1:20 in 100 µl of buffer. The reaction was allowed to proceed overnight at 37° C. after which a second addition of protease was added (protease to substrate ratio of 1:20) and incubated at 37° C. for a further 4 hours. The peptides were analysed by Tricine SDS/PAGE as described for Lysobacter protease-C.

Cyanogen bromide (CNBr) cleavage of lysozyme

Fragmentation was performed in 70% formic acid with a protein concentration of 5 mg ml$^{-1}$ and a CNBr:methionine ratio 100:1. The reaction mixtures were left in the dark, under nitrogen, at room temperature, for 24 hours. The reaction mixture was lyophilised before further analysis.

Electrophoresis

SDS/PAGE (sodium dodecyl sulphate/polyacrylamide gel electrophoresis) was conducted as described by Laemmli [Nature 227, 680–685 (1970)]. Tricine SDS/PAGE was conducted according to the method of Schagger and von Jagow [Anal Biochem 166, 368–379 (1987)] using a 16.5% T and 3% C resolving gel, 10% T, 3% C spacer gel and 4% T, 3% C stacking gel.

Mini gels (100×80×0.75 mm, supplied by Sigma Chemical Co) were used for resolving peptide fragments. The gel was cast 24 hours prior to use and equilibrated overnight at 4° C. Pre-electrophoresis was conducted at 6 mA for 2 hours with an anode buffer containing 100 µM reduced glutathione and subsequently run with 50 µM mercaptoacetic acid in the buffer to decrease N-terminal blocking. Approximately 350 pmoles of protein was loaded per well and electrophoresed using a current of 10 mA until the tracking dye had entered the stacking gel and then at 20 mA through the separating gel. Proteins were transferred onto PVDF (polyvinylidene difluoride) membranes as described by LeGendre et al [A Practical Guide to Protein and Peptide Purification for Microsequencing (Matsudaira, P, ed) pp53–57, Acedemic Press Inc, London (1989)] using a Trans-Blot SD Cell (Bio-Rad). A constant current of 500 mA was applied for 20 minutes at 20° C.

Sequence analysis

Lysozyme fragments were sequenced using an Applied Biosystems 470A gas phase sequencer employing immobilisation on PVDF membranes or on polybrene treated glass fibre discs for shorter peptides. Amino acids were identified as their phenylthiohydantoin (PTH) derivatives by on-line analysis on an ABI 120A HPLC. PTH derivatives were quantified by their $A_{269}$ using authentic standards. The elution position of 3-nitrotyrosine was determined by direct application of 3-nitrotyrosine (approximately 0.1 µg) to a pretreated glass fibre disk followed by repeated Edman degradation cycles. The elution position of 3-nitrotyrosine PTH derivative was based on the appearance of a large peak not present in the standard set of PTH derivatives, which rapidly decreased in quantity during subsequent cycles.

Fluorescamine Assay

To assay for primary amine groups, 0.1 to 2 µg of lysozyme in 200 µl of water was added to 2.1 ml of 0.1M sodium tetraborate solution (pH 9.5), and 200 µl of a 0.03% (w/v) fluorescamine solution in acetonitrile was added and mixed. The fluorescence was recorded with an excitation wavelength of 380 nm and emission of 465 nm using a Perkin Elmer LS50 fluorescence spectrophotometer.

Scanning Densitometry

Scanning densitometry was done using a Pye Unicam SP1800 ultraviolet spectrophotometer.

UV/visible spectroscopy

UV/visible spectroscopy was performed using a Shimadzu UV2100 spectrophotometer. Spectroscopic titrations were recorded with a lysozyme concentration of $1\times10^{-5}$M in 1 mM sodium phosphate pH 10. The pH of the solution was gradually decreased by the addition of small aliquots of concentrated HCl with a capillary pipette, and the absorbance at 428 nm recorded.

Reaction with sodium dithionite 3-nitrotyrosine was reduced by incubation with a 20 fold molar excess of sodium dithionite in 100 mM Tris/HCl pH 8.0 for 10 minutes at room temperature.

Reaction of reduced lysozyme with FITC

100 µg of lysozyme was reduced as described above, and excess reagents removed by gel filtration on a Biogel P6 column equilibrated with 0.1 M sodium acetate buffer pH 5.0 and eluted with the same buffer. The protein was recovered from the column and incubated with 5 µl of FITC (fluorescein isothiocyanate) solution (2 mg in 1 ml of abs. ethanol), for 30 minutes at room temperature. Protein was recovered by reversed phase h.p.l.c. using the same procedure described for peptide mapping. Purified protein was lyophilised, dissolved in 0.1 M Tris/HCl pH 8.0 and the UV/visible spectra recorded.

Measurement of enzyme activity

Enzyme activity was measured using a bacterial cell wall assay with *Micrococcus lysodeikticus* as the substrate. The change in attenuation at 450 nm was recorded in 0.066M potassium phosphate buffer pH 6.25, 25° C. One unit is defined as the amount of enzyme that causes a change in attenuation of $1\times10^{-3}$ absorbance units min$^{-1}$ in 2.6 ml of a suspension of cell walls (0.15 mg ml$^{-1}$), pH 6.25.

Results

Anodic reactions of proteins in alkaline buffers

Figure 1:
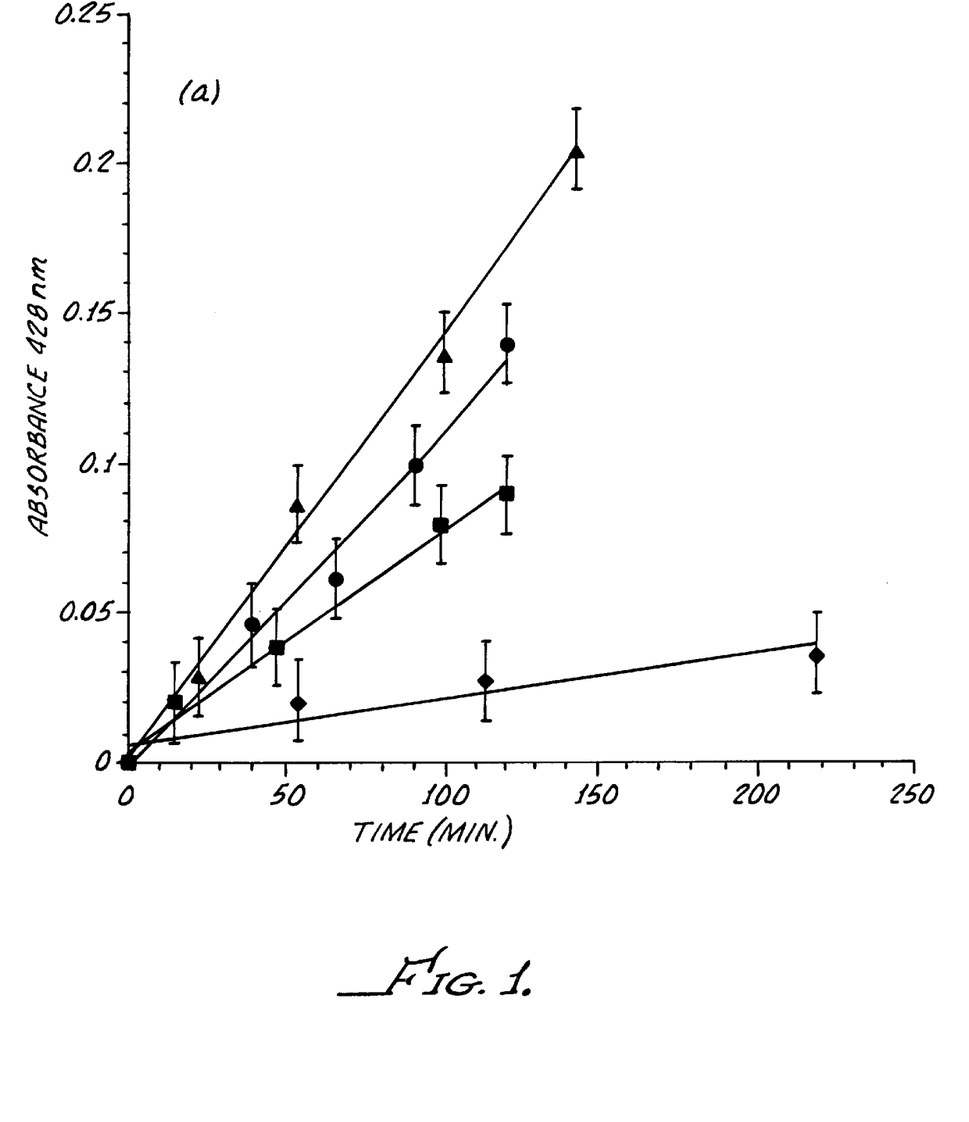
FIG. 1 shows the effect of potential on the rate of chromophore production in the electronitration of lysozyme.

Electrooxidation of BSA (bovine serum albumin), ribonuclease A, subtilisin and hen egg white lysozyme in alkaline buffers was found to produce a yellow colouration in the reaction mixture. This was particularly noticeable at copper electrodes in 50 mM sodium tetraborate solution (pH approximately 9.5) with a controlled current of between 1 to 40 mA (2 cm×2 cm electrodes), or at fixed potentials of between 1.0 and 1.6V vs SCE. The chromophore has a maximum absorbance at 428 nm at pH 8.0. Lysozyme was selected as the protein for subsequent analysis and characterisation of this chromophore. The increase in absorbance at 428 nm was used to quantify the production of the chromophore in a series of experiments conducted under potentiostatic control (FIG. 1). It is apparent that the rate of reaction decreases when the potential is raised above 1.2V.

Characterisation of the chromophore

The yellow chromophore produced from a typical reaction ie 1.2V, 90 min, 0.1% lysozyme in 50 mM sodium tetraborate, was not dialysable. Analysis by gel filtration showed the yellow species co-eluted with lysozyme. Furthermore, SDS/PAGE on a 15% polyacrylamide gel showed the yellow species had the same apparent molecular mass as lysozyme and could be seen as a yellow band on the gel. It appeared that this chromophore was associated with the protein and was due to a covalent modification. This was investigated further by purifying the modified forms of lysozyme, subjecting these to peptide mapping and sequencing any modified peptides to asses changes in the primary structure of the protein and locate the positions of the modifications.

Purification of modified lysozyme

Figure 2:
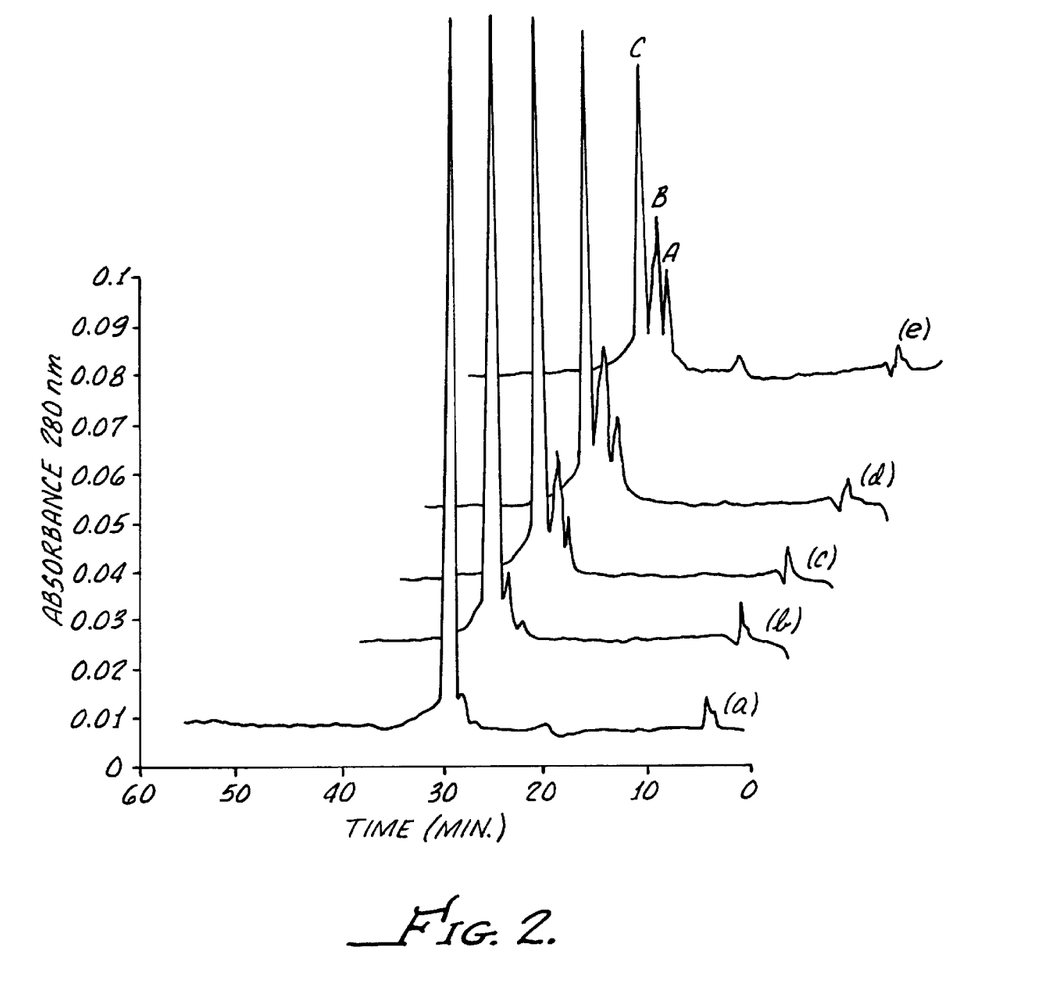
FIG. 2 shows the ion exchange h.p.l.c. of electrochemically modified lysozyme after (a) 0, (b) 23, (c) 53, (d) 99 and (e) 143 minutes of reaction.

Fractionation of electrooxidised lysozyme, during the course of a reaction, by cation exchange h.p.l.c. revealed three species, A, B and C, as shown in FIG. 2. Species C eluted with native lysozyme while B and A eluted ahead of native lysozyme (ie they have a lower pI). The decrease in native protein and production of species A and B was found to correlated with the appearance of the yellow chromophore, thus the two appeared to be linked.

Fractions corresponding to species A, B and C were pooled, dialysed against distilled water, analysed by SDS/PAGE and cell wall lytic activity measured. Analysis by SDS/PAGE showed that A,B and C had the same apparent molecular mass as lysozyme and cell wall lytic activity was detected in all three samples.

Limited proteolysis of A, B and C with Lys-C protease followed by Tricine SDS/PAGE revealed peptide maps. This indicated that lysine had not been oxidised and permitted the use of a fluorescamine assay to quantify amine groups and provided an accurate quantification of the amount of protein. A summary of the quantitative data from uv/vis spectroscopy, weak cation exchange chromatography and cell wall lysis is given in Table 1. It can be seen from the table that the protein with the lowest pI (A) contained twice the molar amount of chromophore as species B, and species C contained no yellow chromophore. The enzyme activity was also found to decrease according to the degree of modification.

Sequence analysis of modified lysozyme

Figure 3:
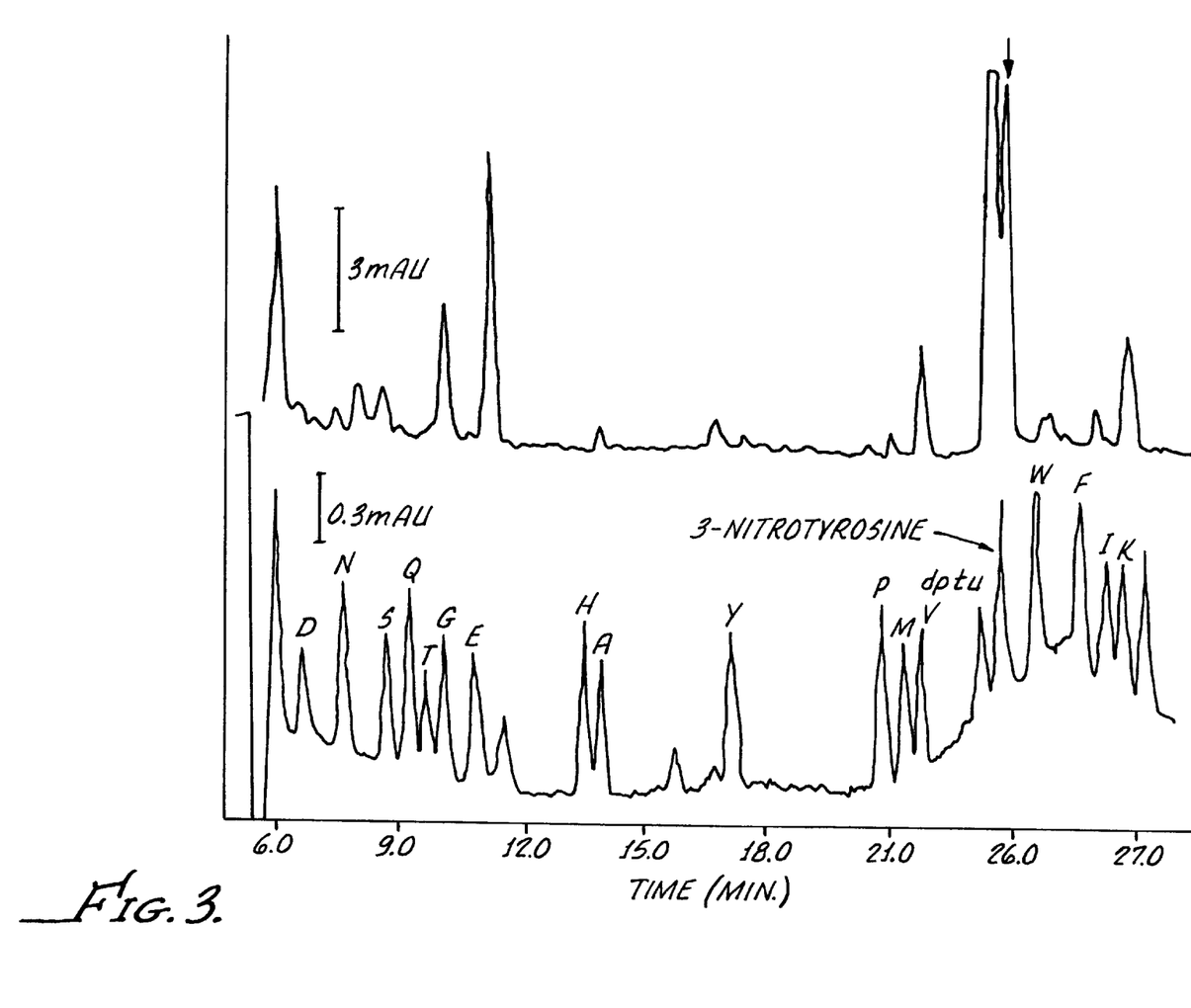
FIG. 3 shows the identification of 3-nitrotyrosine by microsquencing (the reversed phase h.p.l.c. analysis of the PTH derivative of residue 23 from species B is shown in the upper trace; the new peak due to nitrotyrosine is arrowed. The lower trace shows a 6 pmol mixture of standard amino acids including 3-nitrotyrosine).

Analysis of tryptic peptides from B, by reversed phase h.p.l.c. shows a nearly identical profile to that of native lysozyme. However, an extra peak appeared in the modified lysozyme digest which bears the yellow chromophore. Sequence analysis showed this to be the peptide corresponding to residues Gly-22-Lys-33 of lysozyme except for a very low yield of tyrosine at position 2 (Tyr-23 of lysozyme). The absence of a peak corresponding to the PTH derivative of tyrosine coincided with the appearance of a novel peak which eluted just after N,N'-diphenylthiourea (FIG. 3).

It appeared that tyrosine modification was responsible for the production of the yellow chromophore and the pI change in electrosynthetically modified lysozyme. Lysozyme contains three tyrosine residues (20,23,53) of which 20 and 23 are in a partially exposed loop region consisting of residues 17-23. Digestion with V8 protease hydrolyses the protein at Glu-35 and Glu-7. The fragment 36-129 is easily resolved by Tricine SDS/PAGE and allows independent analysis of Tyr-53. Scanning densitometry of V8 digests of A and B separated by Tricine SDS/PAGE showed that residues 36-129 contained no 428 nm absorbing species. All the chromophore was contained within the first 35 residues showing that modification of tyrosine residues in the loop region 17-23 was responsible for the chromophore in the intact protein. As species A contains twice the molar amount of chromophore than species B it seemed that A was modified at both Tyr-20 and Tyr-23. To further confirm this CNBr peptide 13-105 (lysozyme contains two methionine residues at residues 12 and 105) was prepared and analysed by N-terminal sequencing. Preparation of this peptide for species A, B and C, separation by SDS/PAGE and electroblotting onto PVDF membranes followed by sequencing allowed analysis of the loop 17-23 and provided quantitative analysis of the degree of modification. Analysis revealed that species A gave very low yields of PTH tyrosine and the presence the modified PTH tyrosine at both positions 20 plus 23. Species B was found to be modified at tyrosine 23 with no modified PTH tyrosine peak at position 20, confirming the proteolytic digest and spectroscopic data.

Identification of the chromophore

The chromophore produced during this study is similar to that of 3-nitrotyrosine. Furthermore, during the sequence analysis of tryptic peptide T4, Tyr-23 was replaced by a peak eluting after N,N'-diphenylthiourea. This new product had the same retention time as authentic 3-nitrotyrosine.

Reduction of nitrotyrosine with sodium dithionite yields 3-aminotyrosine, the amine group of which has a low pKa (4.7). Thus, this group will be deprotonated at a lower pH than any other amine in the protein. Selective modification of 3-aminotyrosine can be achieved by conjugation with an amine reactive probe at low pH. Reaction of dithionite reduced lysozyme with FITC at pH 5.0 clearly showed a specific labelling of the reduced, nitrated lysozyme. The labelled protein was further characterised by peptide mapping. The fragments Ser 36 to the C-terminal (V8 digest), and Lys 13 to Met 105 (cyanogen bromide cleavage) were prepared, and separated by Tricine SDS/PAGE. This located the bulk of the fluorescent label to between residues 13-36. Site-specific labelling of reduced, nitrated Tyr 20 and Tyr 23, or Tyr 23 alone, appears to have been achieved.

Discussion

This example demonstrates that BSA, ribonuclease A, subtilisin and lysozyme can be electrochemically transformed. Moreover, in lysozyme the modification may be specific to tyrosine residue 23. Tyr-53 was not modified and independent modification of Tyr-20 was not observed. Modification of Tyr-23 must therefore be a prerequisite for the modification of Tyr-20. The indication from UV/visible spectroscopy, spectral titrations, $pK_a$, chemical reaction with dithionite and reverse-phase h.p.l.c. of the PTH derivative of the modification product strongly suggest that it is 3-nitrotyrosine.

Reduction of 3-nitrotyrosine to the corresponding colourless aminophenol, using sodium dithionite, produces an amine moiety capable of selective modification with a variety of reagents at low pH. This offers a novel possibility of labelling or immobilising lysozyme at a specific site.

EXAMPLE 2

Electrooxidation of Methionine

CNBr fragmentation of lysozyme

Methionine is an electroactive amino acid. Peptides containing methionine can be specifically cleaved by cyanogen bromide under acidic conditions. Oxidised methionine is refractory to cleavage by CNBr. Different fragmentation patterns will therefore be produced upon oxidation of methionine.

Lysozyme contains two methionine residues (12 and 105). A total of five fragments will be generated depending upon the extent of CNBr fragmentation, viz CN(2,3) [uncut at M105], CN(1,2) [uncut at M12], CN2 [13-105], CN3 [106-129], and CN1 [1-12].

Incomplete fragmentation in 20% formic acid showed that partial fragments CN(1,2) and CN(2,3) could be resolved by Tricine SDS/PAGE employing a 16.5% T, 3% C resolving gel. The gel could be subsequently analysed by scanning densiotometry to provide a quantitative analysis of the composition of each peptide. Any changes in the fragmentation pattern produced by oxidation could then be readily analysed.

Electrochemical oxidation of methionine

Electrooxidation reactions were performed on hen egg white lysozyme (HEWL) to investigate if changes in CNBr fragmentation patterns could be observed. Initial investigations were performed in 0.1 M Briton-Robinson buffers (0.1M acetic acid, 0.1M phosphoric acid, 0.1M boric acid titrated to required pH with sodium hydroxide) at pH 2.5, 6.0 and 10.5. Graphite electrodes were used.

Reactions were performed at a constant current density of 5 mA/cm$^2$. The use of galvanostatic control allowed direct comparison of reaction in terms of number of electrons passed and time. Aliquots were removed at various time intervals and immediately precipitated with trichloroacetic acid, followed by CNBr fragmentation.

Effect of pH on the electrooxidation of methionine

At low pH (pH 2.5) a noticeable change in the fragmentation pattern was observed during the oxidation of lysozyme. Visual inspection of the SDS gel slab revealed a clear increase in amount of peptide CN(2,3) with time. This indicates a specific oxidation of Met-105 at pH 2.5. At pH 6 and 10.5 no significant electrooxidation of methionine was observed. There was a residual amount of unfragmented protein (10%±1.5) observed during sample preparation; reactions performed in the absence of current, and allowing samples to stand after partial oxidation, caused no change in the fragmentation pattern.

Figure 4:
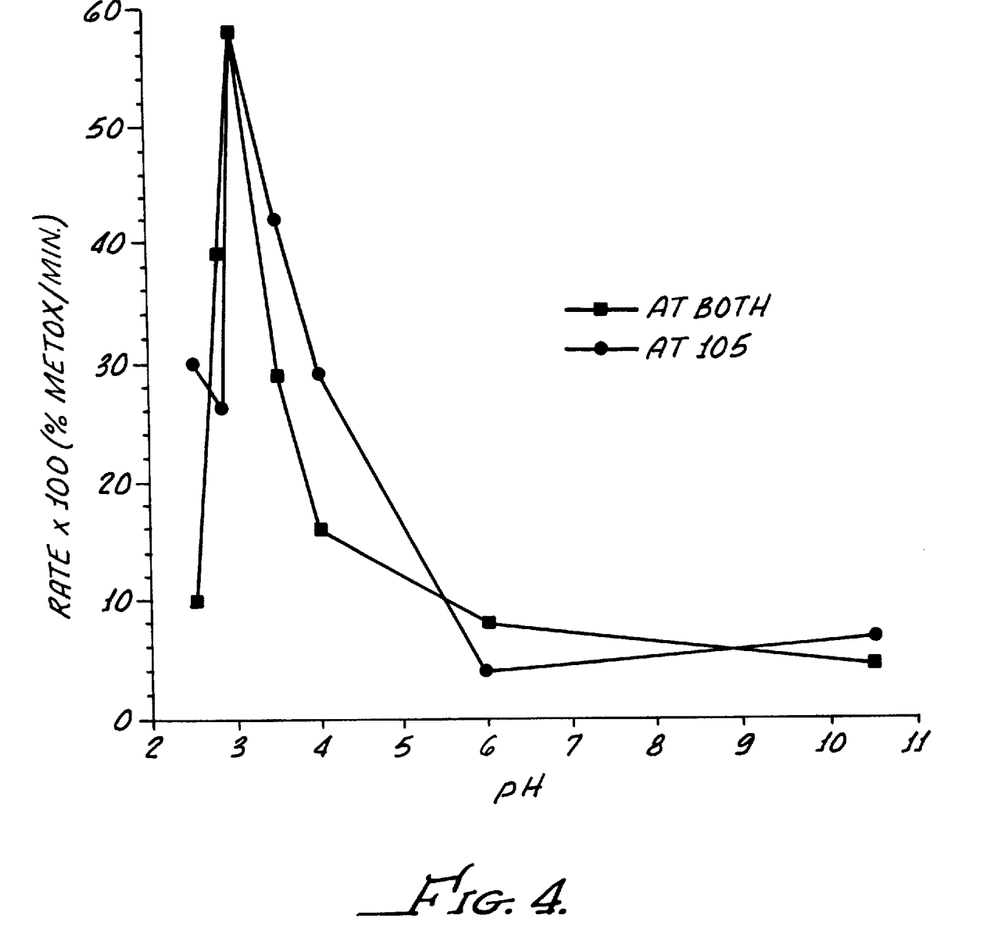
FIG. 4 shows the relative rate of methionine oxidation as a function of pH.

Scanning densitometry of the gel showed an increase in CN(2, 3) and unfragmented lysozyme with a concomitant decrease in CN2 and CN1+CN3. This confirmed that oxidation of Met-105 or Met-105 plus Met-12 occurred with a corresponding decrease in unfragmented lysozyme. A plot of Δ peak area vs time exhibited an initially linear relationship for all peptides. Linear regression analysis was subsequently employed to give Δ peak area [CN(2,3)] min$^{-1}$ and Δ peak area [unfragmented lysozyme] min$^{-1}$. This was extended across the pH range 2.5–10.5 and expressed as a relative rate of oxidation (FIG. 4). During the oxidation reactions and SDS/PAGE analysis the total amount of Coomassie Blue stained protein remained constant, consequently changes in the binding of this dye during the reaction was not a source of error. The rate of oxidation of Met-105 and Met-105 plus Met-12, at a current density of 5 mA/cm$^{-2}$, show the same general trend. There were noticeable maxima for the above peptides at pH~3, decreasing rapidly either side of this.

Summary

Oxidation of lysozyme in 0.1 M Briton-Robinson buffer at pH 2.5–10.5 showed a maximum rate at pH 3.0. There was a selective oxidation at Met-105, or at both Met-12 and Met-105, depending upon choice of electrochemical reaction conditions. No significant independent oxidation of Met-12 was observed.

Additional factors affecting the electrooxidation of methionine in HEWL

Effect of acetonitrile

Figure 5:
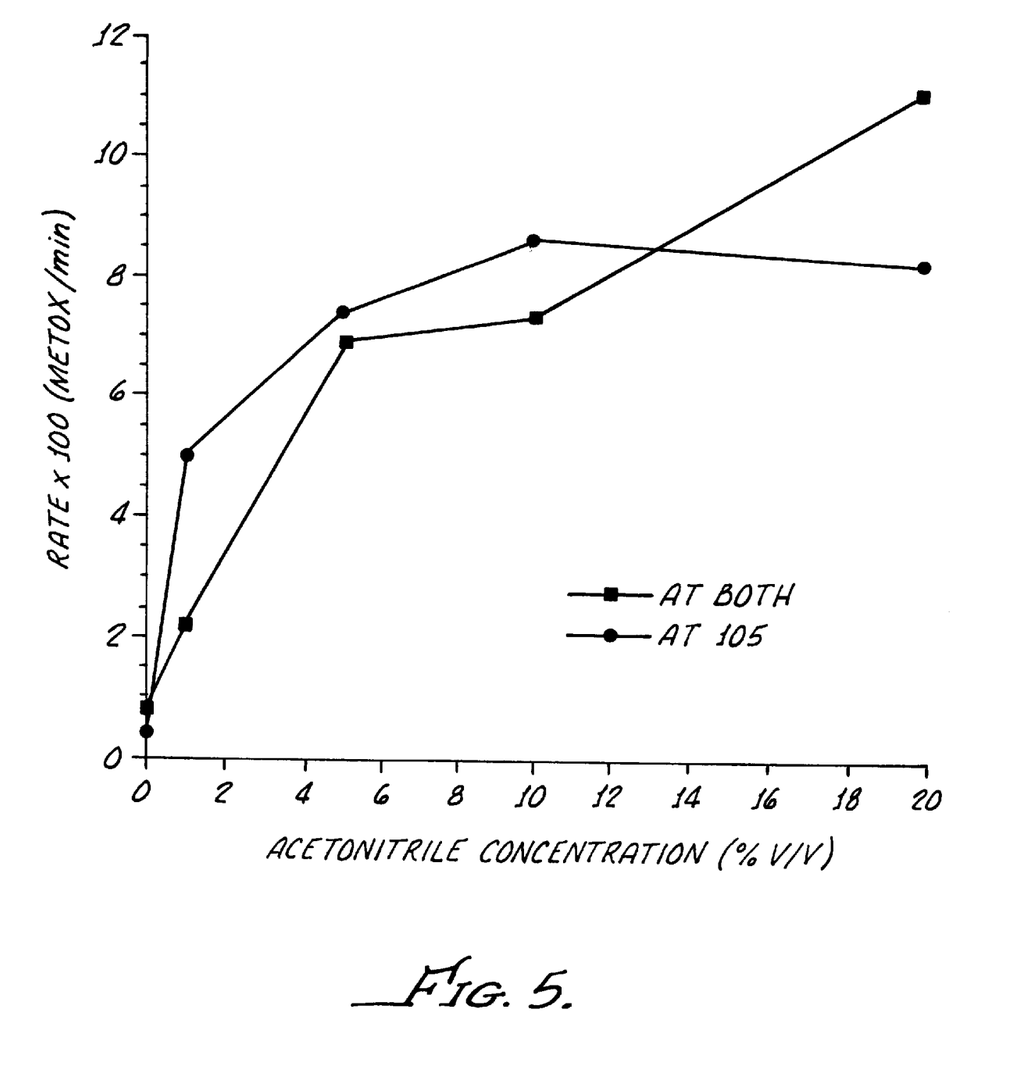
FIG. 5 shows the relative rate of methionine oxidation at pH 6.0 as a function of acetonitrile concentration.

The effect of increasing acetonitrile concentration (0–20% v/v), at pH 6.0, was seen to cause an increase in the rate of electrooxidation (FIG. 5). Moreover, increasing acetonitrile concentration decreases the selectivity (Met-105 oxidation/Met-12 plus Met-105 oxidation).

Effect of potential

Reactions were performed at pH 3.1 in 0.1 M Briton-Robinson buffer employing a divided cell. The results are summarised in Table 2. There was no observed oxidation at potentials of 1.0 V $E_{SCE}$ and less. The specificity of the reaction was found to decrease with increasing anode potential. This is illustrated in FIG. 6 with the scanning densitomograms of SDS/PAGE sample at 1.3V and 1.0V $E_{SCE}$. Oxidation at 1.3 V was seen to produce an increase in CN(2,3), whereas oxidation at 1.5 V caused an increase in both unfragmented product and CN(2,3). Furthermore, the amount of oxidised protein CN1 was at a maximum at 1.3 V, and decreased rapidly above this potential.

Table 1 shows the properties of the products obtained by electrochemical modification of lysozyme as described in Example 1.

TABLE 1

| Protein Species | $\epsilon_{280}M^{-1}cm^{-1}$ | $\epsilon_{428}M^{-1}cm^{-1}$ | Specific activity | pI |
|---|---|---|---|---|
| A | 5.5 × 10$^4$ | 8.4 × 10$^3$ | 39700 ± 940 | 10.7 |
| B | 5.5 × 10$^4$ | 4.2 × 10$^3$ | 47900 ± 960 | 10.8 |
| C | 3.9 × 10$^4$ | 0 | 50700 ± 1020 | 11.0 |
| native | 3.9 × 10$^4$ | 0 | 51500 ± 1030 | 11.0 |

Table 2 shows the effect of potential on the electrochemical modification of lysozyme as described in Example 2.

TABLE 2

| potential | % oxidised/min | | % oxidised/coulomb | |
|---|---|---|---|---|
| V $E_{SCE}$ | Met 105 | Met 105 + 12 | Met 105 | Met 105 + 12 |
| 0.8 | 0 | 0 | 0 | 0 |
| 1.0 | 0 | 0 | 0 | 0 |
| 1.3 | 0.07 | 0.02 | 11.4 | 3.8 |
| 1.5 | 0.02 | 0.11 | 0.29 | 1.7 |
| 1.7 | 0.6 | 0.6 | 0.18 | 0.18 |

We claim:

1. A method for the electrooxidation of one or more pendant groups in a protein molecule comprising a chain of alpha-amino acid monomer residues of general formula —NHCH(R)CO—, wherein R is a pendant group selected from the group consisting of pendant groups of cysteine, cystine, arginine, lysine, tyrosine, tryptophan, histidine, aspartate, glutamate, methionine, serine, and threonine residues, which method comprises the steps of a) forming a solution or dispersion of said protein molecule, b) placing the dispersion or solution so obtained in an electrochemical cell, c) applying an electric potential across said electrochemical cell to form a reaction product in which one or more pendant groups of said protein molecule has been electrooxidized, and d) recovering said reaction product.

2. A method as claimed in claim 1, which is carried out at a potential relative to a standard calomel electrode (SCE) of from 0.6 to 3.0 V.

3. A method as claimed in claim 2, which is carried out at a potential of from 0.9 to 1.7V SCE.

4. A method as claimed in claim 1, which is carried out under acidic conditions and which results in oxidation of methionine monomer residues.

5. A method as claimed in claim 4, which is carried out using graphite electrodes.

6. A method as claimed in claim 4, which is performed at a pH of between 2 and 5.

7. A method as claimed in claim 6, which is performed at a pH of between 2 and 4.

8. A method as claimed in claim 4 which is carried out at a potential of greater than 1.0 V SCE.

9. A method as claimed in claim 1, wherein the protein molecule is an enzyme.

10. A protein having one or more pendant groups modified by the method of claim 1.

* * * * *